(12) United States Patent
Divi et al.

(10) Patent No.: US 8,884,004 B2
(45) Date of Patent: Nov. 11, 2014

(54) PROCESS FOR THE PREPARATION OF SUCRALOSE

(75) Inventors: Murali Krishna Prasad Divi, Hyderabad (IN); Gundu Rao Padakandla, Hyderabad (IN); Mysore Aswatha Narayana Rao, Hyderabad (IN); Shaik Nowshuddin, Hyderabad (IN)

(73) Assignee: Divi's Laboratories, Ltd. (IN)

( * ) Notice: Subject to any disclaimer, the term of this patent is extended or adjusted under 35 U.S.C. 154(b) by 586 days.

(21) Appl. No.: 13/291,212

(22) Filed: Nov. 8, 2011

(65) Prior Publication Data
US 2013/0060018 A1 Mar. 7, 2013

(30) Foreign Application Priority Data

Sep. 2, 2011 (IN) ............................. 3024/CHE/2011

(51) Int. Cl.
*C07H 3/04* (2006.01)
(52) U.S. Cl.
CPC ........................................ *C07H 3/04* (2013.01)
USPC ................................. 536/124; 514/53; 127/41
(58) Field of Classification Search
CPC .......................... C07H 3/04; A23V 2250/264
USPC .................................. 536/124; 514/53; 127/41
See application file for complete search history.

(56) References Cited

U.S. PATENT DOCUMENTS

| 2,421,380 | A | * | 6/1947 | Horace ........................... 127/63 |
| 4,380,476 | A | | 4/1983 | Mufti et al. |
| 4,617,269 | A | | 10/1986 | Rathbone et al. |
| 4,889,928 | A | | 12/1989 | Simpson |
| 4,980,463 | A | | 12/1990 | Walkup et al. |
| 5,498,709 | A | | 3/1996 | Navia et al. |
| 7,838,642 | B2 | | 11/2010 | Wang et al. |
| 2007/0207246 | A1 | | 9/2007 | Wang et al. |
| 2008/0103298 | A1 | | 5/2008 | Ho et al. |
| 2008/0300401 | A1 | | 12/2008 | Xu |
| 2009/0227783 | A1 | | 9/2009 | Hao |

OTHER PUBLICATIONS

Roger Adams and B. K. Brown, Hydrazine Sulfate, Organic syntheses, Coll. vol. 1, p. 309(1941); vol. 2, p. 37 (1922).

* cited by examiner

*Primary Examiner* — Patrick Lewis
*Assistant Examiner* — Everett White
(74) *Attorney, Agent, or Firm* — Caesar, Rivise, Bernstein, Cohen & Pokotilow, Ltd.

(57) ABSTRACT

The present invention provides a method for preparing colorless sucralose, wherein 4,1',6'-trichloro-4,1',6'-trideoxy-galactosucrose-6-acetate containing colored impurities formed during chlorination of sucrose-6-acetate is treated with sodium hypochlorite, where sodium hypochlorite acts both as a decolorizing agent and as a reagent for the ester hydrolysis.

7 Claims, No Drawings

PROCESS FOR THE PREPARATION OF SUCRALOSE

CROSS-REFERENCE TO RELATED APPLICATION

This application claims priority from India Application 3024/CHE/2011, filed Sep. 2, 2011, entitled Process for the Preparation of Sucralose, which application is assigned to the same assignee as this application and whose disclosure is incorporated by reference herein.

FIELD OF INVENTION

The present invention relates to an improved process for the preparation of colorless sucralose.

BACKGROUND OF THE INVENTION

Sucralose (4,1',6'-trichloro-4,1',6'-trideoxy-galactosucrose, or 1,6-dichloro -1,6-dideoxy-β-D-fructofuranosyl-4-chloro-4-deoxy-α-D-galactopyranoside) is an artificial sweetener derived from sucrose. It is about 600 times sweeter than cane sugar. It is considered safe because it is excreted in humans without undergoing any metabolism. It has high resistance to acid hydrolysis and is highly stable to heat. Because of these advantages, sucralose is one of the most widely used sweeteners in the market.

Synthesis of sucralose involves substitution of two primary alcohol groups at the 1' and 6' positions and a secondary alcohol group at the 4 position with chlorine. During the chlorination (for the sake of simplicity this reaction will be referred henceforth as 'chlorination') the other primary alcohol group at the 6-position should not be affected. This is generally achieved by selective esterification of a primary alcohol at the 6 position before chlorination. Finally the ester is hydrolyzed to obtain sucralose.

The Tate & Lyle group has developed a method for the preparation of sucrose-6-acetate selectively through an ortho ester intermediate (U.S. Pat. No. 4,889,928).

Chlorination of sucrose-6-acetate is a typical $S_N2$ substitution reaction resulting in inversion of the configuration at the 4-position. Because of this inversion, the glucose ring gets converted to a galactose ring. Thus, trichlorination of sucrose-6-acetate gives 4,1',6'-trichloro-4,1',6'-trideoxy-galactosucrose-6-acetate (TGS-6-acetate) In most cases, a Vilsmeier type reagent is preferred for the trichlorination of sucrose-6-acetate (U.S. Pat. Nos. 4,380,476; 4,617,269; and 4,980,463). U.S. Pat. No. 4,980,463 describes the use of a Vilsmeier reagent prepared from phosgene and dimethylformamide (DMF) for the chlorination of sucrose-6-acetate. Triphosgene, which is a safer alternative to phosgene, has been used for the preparation of a Vilsemeier reagent from DMF. (US 2008/0103298 A1). Chlorination of sucrose-6-ester with a Vilsmeier reagent is a complex reaction. For the chlorination at all three positions, a temperature of about 100-120° C. is required and the reaction is to be maintained at this temperature for several hours. The severe conditions required for complete chlorination results in a dark brown to black reaction mass. Irrespective of the workup methods, the TGS-6-acetate is always obtained as a highly colored product. Almost all reported methods describe the use of activated charcoal for the decolorization (US 2007/0207246A1; US 2008/0300401 A1; US 2008/0103298A1). US application US 2007/0207246A1 describes a process where TGS-6-acetate was decolorized using activated charcoal and after ester hydrolysis, the final sucralose product needed to be again decolorized using charcoal. The application US 2008/0300401A1 describes a process where TGS-6-acetate was decolorized twice using activated charcoal and after ester hydrolysis, the final sucralose product was again decolorized using charcoal for a third time.

TGS-6-acetate is hydrolyzed to sucralose using a base such as sodium methoxide (U.S. Pat. No. 4,380,476, US 2009/0227783), sodium hydroxide (U.S. Pat. No. 5,498,709), potassium hydroxide (US 2007/0207246) or an organic base such as triethylamine (U.S. Pat. No. 7,838,642). When sodium methoxide is used, the conversion remains incomplete. Hydrolysis using organic base is also slow and the acetate salts of the organic bases formed in the reaction have similar solubility as sucralose and their removal is difficult.

Thus, there is a strong need for an efficient process to decolorize TGS-6-acetate and sucralose. There is also a need for a rapid method for the hydrolysis of TGS-6-acetate to obtain sucralose.

SUMMARY OF THE INVENTION

While exploring various alternatives to the existing cumbersome charcoal treatment for procuring colorless sucralose, we argued that decolorization of TGS-6-acetate followed by hydrolysis may result in a colorless sucralose. We then found that the highly colored TGS-6-acetate, obtained after the chlorination of sucrose-6-acetate, can be completely decolorized by treating it with a sodium hypochlorite solution. Surprisingly, the decolourization process was very rapid, almost instantaneous. As a further surprise, we found that the treatment with sodium hypochlorite also resulted in the hydrolysis of the ester group giving sucralose directly.

Thus, the present invention discloses a process in which the treatment of highly colored TGS-6-acetate with sodium hypochlorite results both in efficient decolourization of TGS-6-acetate and also ester hydrolysis, simultaneously in one step, to give colorless sucralose.

DETAILED DESCRIPTION OF THE INVENTION

According to the present invention, there is provided a process for the preparation of sucralose, which comprises:
  a) reacting sucrose-6-acetate with a Vilsmeier type reagent to obtain 4,1',6'-trichloro-4,1',6'-trideoxy-galactosucrose-6-acetate (TGS-6-acetate); and
  b) treating the TGS-6-acetate so obtained with sodium hypochlorite to obtain colorless sucralose.

The required starting material, sucrose-6-acetate, can be prepared from sucrose as described in U.S. Pat. No. 4,889,928 incorporated y reference in its entirety herein or by any other suitable method. In one aspect of the invention, sucrose-6-acetate is dissolved in a polar solvent and chlorinated using a Vilsmeier type reagent. For this reaction, dimethylformamide (DMF) is the solvent of choice. DMF not only generates a Vilsmeier reagent with a chlorinating agent, but also is a good solvent for sucrose-6-acetate. Further, the DMF with its aprotic nature and high boiling point is also a good solvent for the nucleophilic substitution reaction. The chlorinating agent for the preparation of the Vilsmeier reagent from DMF can be thionyl chloride, phosphorus oxychloride (POC13), oxalyl chloride, phosgene, triphosgene and the like. Phosphorus oxychloride is expensive while oxalyl chloride decomposes to poisonous carbon monoxide. When thionyl chloride/DMF is used for the generation of the Vilsmeier reagent, a high amount of charred material is observed at higher temperature. Phosgene is highly poisonous and being a gas, difficult to handle on a large scale. Triphosgene, which is a solid and a safer alternative to phosgene, is preferred. Using the Vilsmeier reagent prepared from triphosgene/DMF results in efficient and complete chlorination. Addition of triphosgene to a solution of sucrose-6-acetate in DMF results in a highly exothermic reaction. Cooling of sucrose-6-acetate solution to −10° C. and gradual addition of triphosgene as a solution helps in controlling the exothermic reaction. On addition, a Vilsmeier type salt or N,N-dimethylchloroforminium chloride is formed which is poorly soluble at low temperatures. Stirring of the resulting suspension should be efficient to prevent settling down of the reagent. Improper stirring results in poor yields. The temperature of the reaction is gradually raised. At about 80° C., the reaction mixture is a clear solution, but is colored. The temperature is further raised to 115±5° C. During this stage the solution turns dark brown to black. The reaction has to be maintained at this temperature for 4 to 6 hours for complete chlorination. After completion of the reaction, the reaction mixture is cooled to about 0° C. and neutralized to pH 7.0 with ammonium hydroxide to decompose excess triphosgene. Most of the solvent is removed by distillation under reduced pressure at 60-65° C. The crude oily syrup obtained is dissolved in water and extracted with an organic solvent such as ethyl acetate. Evaporation of solvent under reduced pressure results in crude TGS-6-acetate as a black oily material. It is dissolved in a water miscible solvent, cooled to 0° C. and treated with a solution of sodium hypochlorite. The water miscible solvent can be an alcohol or an aprotic solvent. The alcohol can be methanol, ethanol, propanol and the like, and the aprotic solvent can be tetrahydrofuran, dioxane, DMF, dimethylsulfoxide (DMSO) and the like. Out of all the solvents tried, methanol was found to be ideal. When water was used, the yields were low. Sodium hypochlorite solution of about 15% w/v strength was prepared according to *Org. Syn. Coll. Vol.*1, 1941, 309-310. Sodium hypochlorite solution is added till the reaction mixture is alkaline (pH>12.0±0.5). On addition of the sodium hypochlorite solution, the black reaction mixture turns colorless. The decolourization is instantaneous and takes place within a few minutes. Simultaneously, the process of ester hydrolysis also starts and formation of sucralose can be detected by TLC using chloroform: methanol (5:1) as a solvent system and sulphuric acid spray for detection. The hydrolysis step is slow and maximum yields are obtained after about 4.0±0.5 hours. Longer periods did not improve the yields. About 10% starting material still remains, which can be recovered during the workup and reused. As the reaction progresses, the pH decreases and more sodium hypochlorite solution is added to maintain the pH at 12.0±0.5. If the pH is not maintained, the yields will decrease. The reaction temperature also plays an important role. At low temperatures (0±5° C.), the reaction goes smoothly and gives the best results. At ambient (25±5° C.) and higher temperatures, consumption of sodium hypochlorite increases many folds and the purity of sucralose obtained also is affected. After the reaction, the pH is adjusted to 7.0 using an acid such as acetic acid and all solvents are removed under reduced pressure at 45-50° C. The colorless solid so obtained is dissolved in water. From the aqueous solution, unreacted TGS-6-acetate can be recovered by extracting with methylene chloride or methyl tert-butyl ether. Sucralose is obtained by extracting the aqueous solution with ethyl acetate. Sucralose thus obtained is a foamy colorless solid containing a high amount of moisture. Recrystallization using n-butyl formate gives white crystalline sucralose (>99% HPLC) with moisture <0.5%.

The embodiments of the present invention are illustrated in the following examples, which do not in any way limit the scope of the invention.

EXAMPLES

Example: 1

Sucrose-6-acetate (72 g, 0.163 mol) was dissolved in 720 ml DMF and cooled to −10° C. Triphosgene (170.2 g, 0.653 mol) in 960 ml toluene was added drop wise and stirred for 1 hr at −10° C. The reaction mixture was heated slowly and maintained at 115±5° C. for 5 hr. After cooling to 0-5° C., the reaction mixture was neutralized to pH 7.0 with NH$_4$OH solution. Most of the solvent was removed by distillation under reduced pressure at 60-65° C. The black crude syrup obtained was dissolved in 300 ml water. It was extracted with ethyl acetate (100 ml×3). Pooled ethyl acetate layers were concentrated under reduced pressure to get TGS-6-acetate as a black oily material. It was dissolved in 300 ml methanol, cooled to 0-5° C., and treated with a solution of sodium hypochlorite (15%) till the pH was 12.0±0.5. The reaction mixture turned colorless. The reaction was maintained at pH 12.0±0.5 for 4.0±0.5 hours by adding an additional amount of sodium hypochlorite solution. The reaction was neutralized to pH 7.0 using acetic acid. All solvents were removed under reduced pressure at 45-50° C. The colorless solid obtained was dissolved in water (200 ml) and washed with methyl tert-butyl ether (MTBE, 50 ml×3) to remove the unreacted TGS-6-acetate. The aqueous solution was extracted with ethyl acetate (100 ml×3). After drying over Na$_2$SO$_4$, the ethyl acetate layer was concentrated under reduced pressure at room temperature to obtain sucralose as a colorless foamy solid. It was recrystallized using n-butyl formate. Yield: 48 g (64.8%, 99.5% HPLC, 0.3% moisture).

Example: 2

Sucrose-6-acetate (72 g, 0.163 mol) was converted to TGS-6-acetate as in example-1.The black crude syrup of TGS-6-acetate obtained (as in example 1) was dissolved in 300 ml water, cooled to 0-5° C. and treated with a solution of sodium hypochlorite (15%) till the pH is 12.0±0.5. The reaction mixture turned colorless. The reaction was maintained at pH 12.0±0.5 for 4.0±0.5 hours by adding more sodium hypochlorite solution and neutralized to pH 7.0 using acetic acid. Solvents were removed under reduced pressure at 45-50° C., the colorless solid obtained was dissolved in water (200 ml) and washed with MTBE (50 ml×3) to remove the unreacted TGS-6-acetate. The aqueous solution was extracted with ethyl acetate (100 ml×3). After drying over Na$_2$SO$_4$, the ethyl acetate layer was concentrated under reduced pressure at room temperature to obtain sucralose as a colorless foamy solid. It was recrystallized using n-butyl formate. Yield: 31.2 g, (42.2%).

Example: 3

Sucrose-6-acetate (10 g, 0.026 mol) was dissolved in 100 ml DMF. Separately thionyl chloride (42.6 g, 0.35 mol) was dissolved in 50 ml ethylene dichloride. Both solutions were cooled to 0-5° C. The thionyl chloride solution was added slowly to sucrose-6-acetate solution and stirred for one hour. The reaction was heated and maintained at 115±5° C. for about 6 hr till the starting material was completely consumed (TLC). After cooling to 0-5° C., the reaction mixture was neutralized to pH 7.0 with NH$_4$OH solution. Most of the solvent was removed by distillation under reduced pressure at 60-65° C. The crude residue was dissolved in 75 ml water and extracted with 100 ml×2 ethyl acetate. Pooled ethyl acetate layers were concentrated under reduced pressure to get a black oily material and was dissolved in 100 ml methanol, cooled to 0-5° C., and treated with a solution of sodium hypochlorite (15%, 10 ml). After the completion of the reaction, it was processed as in example-1. Yield: 5.3 g, 0.013 mol, (52%).

We claim:

1. A process for the preparation of sucralose comprising:
   a) reacting sucrose-6-acetate with a Vilsmeier reagent prepared from dimethylformamide and a chlorinating agent selected from the group consisting of thionylchloride, phosphorus oxychloride, phosgene and triphosgene to obtain 4,1',6'-trichloro-4,1',6'-trideoxy-galactosucrose acetate (TGS-6-acetate); and
   b) treating the TGS-6-acetate with a solution of sodium hypochlorite to obtain colorless sucralose.

2. A process according to claim 1 wherein the step-b is conducted at a temperature of 0 to 5° C.

3. A process according to claim 1 wherein the step-b is conducted at a temperature of −5 to +30° C.

4. A process according to claim 1 step-b wherein TGS-6-acetate is dissolved in a water miscible solvent selected from the group consisting of water, methanol, ethanol, propanol, dimethylformamide, dioxane, dimethylsulphoxide and tetrahedrofuran.

5. A process according to claim 1 step-b wherein the reaction is maintained at a pH 9 to 14.

6. A process according to claim 1 step-b, wherein the water miscible solvent is methanol.

7. A process according to claim 1 step-b wherein the reaction is maintained at a pH 10 to 12.

* * * * *